United States Patent [19]

Wittmann et al.

[11] 4,387,245
[45] Jun. 7, 1983

[54] PREPARATION OF DIACETONEKETOGULONIC ACID BY OXIDATION OF DIACETONESORBOSE

[75] Inventors: Rolf Wittmann, Mühltal-Traisa; Willi Wintermeyer, Seeheim-Jugenheim; Jürgen Butzke, Dieburg, all of Fed. Rep. of Germany

[73] Assignee: Merck Patent Gesellschaft Mit Beschrankter Haftung, Darmstadt, Fed. Rep. of Germany

[21] Appl. No.: 265,490

[22] Filed: May 20, 1981

[30] Foreign Application Priority Data

May 21, 1980 [DE] Fed. Rep. of Germany ....... 3019321

[51] Int. Cl.³ .............................................. C07C 59/10
[52] U.S. Cl. .................................... 562/587; 562/577; 549/315

[58] Field of Search ............................ 562/577, 587; 260/340.2

[56] References Cited

PUBLICATIONS

Elektrochimia, vol. 6, pp. 897–901 (1972).
Advances in Carbohydrate & Biochemistry, vol. 37, p. 79 (1980).

*Primary Examiner*—Paul J. Killos
*Attorney, Agent, or Firm*—Millen & White

[57] ABSTRACT

A process for preparing diacetoneketogulonic acid comprises oxidizing diacetonesorbose in two or more oxidizing steps using different oxidizing agents in each step. In preferred embodiments the first oxidation is done electrochemically or using air and the second oxidation is via hypochlorite treatment.

5 Claims, No Drawings

PREPARATION OF DIACETONEKETOGULONIC ACID BY OXIDATION OF DIACETONESORBOSE

BACKGROUND OF THE INVENTION

The present invention relates to a process for the preparation of diacetoneketogulonic acid, which is a valuable intermediate product used in the preparation of vitamin C.

As a rule, the starting material used for the preparation of diacetoneketogulonic acid is diacetonesorbose. It can be oxidized to diacetoneketogulonic acid using inorganic oxidizing agents, such as $HNO_3$, $H_2O_2$, $KMnO_4$ or in particular hypochlorite. These processes, however, are disadvantageous since in some cases very large amounts of inorganic salts are formed. These are a considerable load on the waste water.

Recently, therefore, particular interest has been aroused by electrochemical oxidation. This process is particularly advantageous because in addition to the anodic oxidation, hydrogen is generated at the cathode. The latter is required within the framework of the total synthesis of vitamin C. Electrochemical oxidation has, however, the disadvantage that a sufficiently high conversion requires very long electrolysis times and a very large electrode surface. The large electrode surfaces and the short lifetime of the electrodes, due to the long electrolysis times, lead to considerable costs. Moreover, with the very long electrolysis times there is a danger of further oxidation of the product. This affects the yield, which as a rule is lower for electrochemical oxidation than for wet-chemical oxidation.

Oxidation with air or other oxygen-containing gases, acting under catalysis by noble metals, in principle is extremely interesting. However, it is subject to the same disadvantages. Although this oxidizing agent is available in virtually unlimited amounts and therefore can be employed inexpensively, considerable disadvantages result from the long reaction times necessary and the further oxidation of the product which then occurs.

SUMMARY OF THE INVENTION

Accordingly, it is an object of this invention to provide a process for the oxidation of diacetonesorbose which avoids these disadvantages.

Upon further study of the specification and appended claims, further objects and advantages of this invention will become apparent to those skilled in the art.

These objects have been attained, surprisingly, by carrying out the oxidation in several steps and using different oxidizing agents in these steps. The present invention therefore relates to a process for preparing diacetoneketogulonic acid by oxidizing diacetonesorbose in several steps and using different oxidizing agents in these steps.

DETAILED DISCUSSION

It is particularly preferred that the diacetonesorbose first be partially oxidized, either electrochemically or with air, and then be completely oxidized with hypochlorite.

The advantages of this process lie, in particular, in the fact that the overall process can be very much better optimized by means of the multi-step procedure and the use of different oxidizing agents. For example, the initial partial oxidation can be carried out in the optimum range with high diacetonesorbose concentrations. Thereby, a high conversion can be achieved in a relatively short time since, astonishingly, the initial conversion per unit time is very high and virtually no further oxidation of the product takes place. As soon as the reaction passes out of this optimum range, it can be followed by oxidation with a second oxidizing agent, preferably hypochlorite, until conversion of the diacetonesorbose is complete.

Both the electrochemical oxidation of diacetonesorbose and its atmospheric oxidation are known per se. The process of atmospheric oxidation described, for example, in German patent specification No. 935,968, Hungarian patent specification No. 162,772, German Offenlegungsschrift No. 2,123,621 and USSR patent specification No. 137,913, in Liebigs Annalen der Chemie, Volume 558, page 171 et seq. (1947) and in Fortschritte der chemischen Forschung (Advances in Chemical Research), Volume 11, pages 285–374 (1969), all the disclosures of which are incorporated by reference herein, is employed analogously in the present process. However, the oxidation is not taken to 100% conversion of diacetonesorbose but is discontinued at a conversion of 20–95%, preferably 30–80% and in particular 40–70%. The solution is then fed to the residual oxidation step, preferably with hypochlorite, in which all of the diacetonesorbose still remaining is converted.

For electrochemical oxidation, see in general, Elektrochimia Vol. 6, pages 897–901 (1972) and Tetrahedron Vol. 28, pages 37–42 and references cited therein whose disclosure is incorporated by reference herein. As a rule, approximately 10–20% by weight diacetonesorbose solutions are used as the starting material. An alkali metal hydroxide, in particular sodium hydroxide, is generally added to the solutions in such an amount that the reaction mixture always contains about 1.5–2 moles of alkali metal hydroxide per mole of diacetonesorbose.

A direct current of about 0.2–20 A per $dm^2$, preferably 0.5–10 A per $dm^2$ of electrode surface is then conducted through the reaction mixture with good mixing, at a temperature of about 20°–70° C., preferably 30°–55° C. Optionally, further additives can be added, such as, for example, the nickel salts or iron salts described in German Auslegeschrift No. 1,668,203 and German Auslegeschrift No. 2,410,034 or the surfactants described in German Offenlegungsschrift No. 2,505,911, all of whose disclosures are incorporated by reference herein. The cell voltage is about 1.8–3.0 volts, preferably about 2.0–2.7 volts. Nickel electrodes have proven particularly suitable. The electrolysis can be carried out continuously or discontinuously in partitioned or non-partitioned cells.

However, in contrast to the known electrolysis processes, the electrolysis is not taken to 100% conversion of diacetonesorbose. It is discontinued at a conversion of about 40–95%, preferably 60–85%. The solution is then fed to the residual oxidation stage with hypochlorite, in which all of the diacetonesorbose still remaining is converted.

The hypochlorite oxidation is known per se. See, e.g., Journal of the American Chemical Society, Vol. 67 (1945), pages 1031–1032 and Tetrahedron, Vol. 14 (1965) pages 881–883, whose disclosure is incorporated by reference herein. However, in the process of this invention, the reaction is carried out with considerably lower concentrations of diacetonesorbose since a large proportion of the initial amount has already been oxidized to diacetoneketogulonic acid. It was, therefore, questionable whether the hypochlorite oxidation would still start at all with the low residual concentration of diacetonesorbose of about 3–5% by weight. Surprisingly, however, the reaction proceeds smoothly if it is carried out at a temperature of about 40°–80° C., preferably 50°–70° C., with a molar ratio of about 2–8 moles, preferably about 3–5 moles, of hypochlorite per mole of diacetonesorbose. A nickel salt is added as the catalyst. Suitable salts include, for example, the chloride, sulfate or nitrate. Nickel chloride hexahydrate is preferably used and is employed in an amount of about 5–150 g and in particular about 5–40 g per kg of diacetonesorbose. The hypochlorite is preferably sodium hypochlorite in the form of an aqueous solution which contains about 13–16 g of active chlorine per 100 ml.

Under these conditions, the residual oxidation is complete in about 1 hour, after which the reaction solution can be worked up in the conventional manner. For example, the solution can be filtered and the filtrate cooled and acidified with hydrochloric acid to effect precipitation of the diacetoneketogulonic acid. By separating off the crystalline product, diacetoneketogulonic acid can be obtained in a yield of far more than 90% of theory.

Surprisingly, the diacetoneketogulonic acid obtained by the process of this invention is considerably more coarsely crystalline than the diacetoneketogulonic acid obtained by the normal hypochlorite oxidation. This advantageous effect produces a product which can be separated off and dried very much more easily and which then has very good free-flowing characteristics. This surprising difference in the particle size distribution is shown in the figures in the table which follows.

| Particle size (μm) | Hypochlorite oxidation (%) | Process according to the invention (%) |
|---|---|---|
| <20 | 45 | 13 |
| 20–30 | 45 | 20 |
| 30–50 | 10 | 65 |
| 50–100 | — | 2 |
| >100 | — | — |

The diacetoneketogulonic acid obtained in this way can then be further processed in the conventional manner to prepare ascorbic acid. The process of this invention is therefore an advantageous improvement of the total synthesis of ascorbic acid. See, e.g., Advances in Carbohydrate and Biochemistry, Vol. 37 (1980), page 79 and following pages, whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

A mixture of 100 kg of diacetonesorbose solution (45% by weight), 30 kg of sodium hydroxide solution (50% by weight), 0.001 kg of nonylphenol polyglycol ether and 220 kg of water is fed into an electrolysis cell with nickel electrodes. It is electrolyzed at a temperature of 50° C., starting with a current density of about 1,000 A/m$^2$. The current density is reduced down to 400 A/m$^2$ as the oxidation proceeds. When a degree of oxidation of about 77% of the diacetonesorbose employed is achieved, the electrolysis is stopped. 44 kg of sodium hypochlorite solution (containing about 11.4 kg of active chlorine) and 0.92 kg of nickel chloride solution (containing about 24% of NiCl$_2$.6H$_2$O) are added to the approximately 340 kg of solution. The latter has a residual content of about 23% of the diacetonesorbose employed (corresponding to about 30 g/kg of solution). The resultant solution is oxidized for about 1 hour at a temperature which rises to about 70° C. The solution is then filtered, cooled to about 0°–5° C. and acidified to a pH of about 1–2 with hydrochloric acid. The diacetoneketogulonic acid which precipitates out is separated off and air-dried. 46.5 kg (92.5% of theory) of diacetoneketogulonic acid are obtained.

EXAMPLE 2

3 kg of an approximately 13% by weight diacetonesorbose solution is partially oxidized electrochemically, to the extent of 80.3%. 685 ml of sodium hypochlorite solution which contains 92.9 g of active chlorine, and 11 ml of approximately 24% by weight nickel chloride hexahydrate solution are then added. The mixture is stirred at a temperature of about 60°–70° C. until no further hypochlorite is detectable. After working up as in Example 1, 408 g (92.4% of theory) of diacetoneketogulonic acid is obtained.

EXAMPLE 3

1 kg of an approximately 13% by weight diacetonesorbose solution is partially oxidized electrochemically, to the extent of 83.5%. It is then oxidized to completion with 182.2 ml of sodium hypochlorite solution, which contains 14.2 g of active chlorine per 100 ml and 3.6 ml of an approximately 24% by weight nickel chloride hexahydrate solution. After the customary working up, 136.8 g (93.6% of theory) of diacetoneketogulonic acid is obtained.

EXAMPLE 4

6.83 kg of an approximately 13% by weight diacetonesorbose solution is partially oxidized electrochemically to the extent of 95.3%. It is then oxidized to completion with 500 ml of sodium hypochlorite solution, which contains 75.2 g of active chlorine, and 21 ml of an approximately 24% by weight nickel chloride hexahydrate solution. 929 g (90.6% theory) of diacetoneketogulonic acid is obtained.

EXAMPLE 5

1 kg of an approximately 13% by weight diacetonesorbose solution is partially oxidized electrochemically to the extent of 64.6%. It is then oxidized to completion with 254 ml of sodium hypochlorite solution, which contains 39.2 g of active chlorine, and 12 ml of an approximately 24% by weight nickel chloride hexahydrate solution. After the customary working up, 133 g (91% of theory) of diacetoneketogulonic acid is obtained.

EXAMPLE 6

Air is passed for 6 hours into a solution of 1.04 kg of diacetonesorbose in 7 l of water, which has been adjusted to a pH of 9–10 with sodium hydroxide solution and to which 50 g of platinum-on-active charcoal (10% of Pt) have been added. The temperature is 80°-90° C., the pH value being kept constant below 10 by the addition of sodium hydroxide solution. The solution, which is thus oxidized to the extent of 62% is separated from the catalyst by filtration. The residual amount of, in total, 0.7 kg of 50% by weight sodium hydroxide solution is added and, at 50° C., 18 ml of a 28.5% by weight nickel chloride hexahydrate solution is added. The residual diacetonesorbose is oxidized by adding 2.6 kg of hypochlorite solution, which contains about 340 g of active chlorine. After the customary working up, 1.07 kg (91.6% of theory) of diacetoneketogulonic acid is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing diacetoneketogulonic acid comprising oxidizing diacetonesorbose in two steps, first oxidizing electrochemically to a degree of conversion of about 40-95% or first oxidizing with oxygen to a degree of conversion of about 20-95%, and then substantially completely oxidizing the remainder with hypochlorite.

2. A process of claim 1 wherein oxygen is used in the first step and is provided in the form of air.

3. A process of claim 1 wherein the hypochlorite oxidation is carried out at a temperature of 40°-80° C. using 2-8 moles of hypochlorite per mole of diacetonesorbose in the presence of a catalytic amount of a nickel salt.

4. In a process for preparing ascorbic acid using diacetoneketogulonic acid as an intermediate, the improvement wherein the diacetoneketogulonic acid is prepared by the process of claim 1.

5. The diacetoneketogulonic acid prepared by the process of claim 1.

* * * * *